United States Patent [19]

Ha et al.

[11] Patent Number: 5,099,056
[45] Date of Patent: Mar. 24, 1992

[54] PROCESS FOR THE PRODUCTION OF N-SUBSTITUTED-AMINOMETHYLPHOSPHONIC ACID DIALKYLESTERS AND OF THE CORRESPONDING ACIDS

[75] Inventors: Hyun-Joon Ha; Gong-Sil Nam, both of Seoul, Rep. of Korea

[73] Assignee: Korea Institute of Science and Technology, Seoul, Rep. of Korea

[21] Appl. No.: 560,385

[22] Filed: Jul. 31, 1990

[30] Foreign Application Priority Data

Mar. 27, 1990 [KR] Rep. of Korea ............... 4116/1990

[51] Int. Cl.⁵ ..................... C07F 9/38; C07F 9/40
[52] U.S. Cl. ........................ 558/122; 558/166
[58] Field of Search ............... 558/115, 87, 170, 122, 558/166

[56] References Cited

U.S. PATENT DOCUMENTS 4,351,779 9/1982 Maier .................... 558/83
4,442,044 4/1984 Purdam ................... 558/126

OTHER PUBLICATIONS

Ikeda, K. et al., Chem. Pharm. Bull. 29(4), 1156–1159 (1981).

*Primary Examiner*—Mary C. Lee
*Assistant Examiner*—Michael G. Ambrose
*Attorney, Agent, or Firm*—Leydig, Voit & Mayer

[57] ABSTRACT

A process for the production of N-substituted aminoethylphosphonic acid derivatives represented by the formula (I) is disclosed

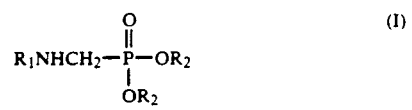

wherein $R_1$ is an alkyl having 1–18 carbon atoms or a cycloolkyl having 3–18 carbon atoms and $R_2$ is hydrogen, methyl or ethyl. This process comprises the steps of: reacting N-alkyl and N-cycloalkylhexahydro-s-triazine of formula

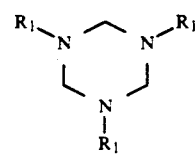

with trialkylphosphites of formula $P(OR_2)_3$ in the presence of titanium tetrahydrochloride at $-20°$–$10°$ C. to yield N-substituted aminomethylphosphonic acid dialkylesters, followed by hydrolysis to yield N-substituted aminomethylphosphonic acid.

3 Claims, No Drawings

PROCESS FOR THE PRODUCTION OF N-SUBSTITUTED-AMINOMETHYLPHOSPHONIC ACID DIALKYLESTERS AND OF THE CORRESPONDING ACIDS

BACKGROUND OF THE INVENTION

The present invention relates to a new process for the production of N-substituted aminomethylphosphonic acid derivatives represented by the formula (I)

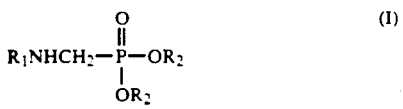

wherein $R_1$ is an alkyl having 1-18 carbon atoms or a cycloalkyl having 3-18 carbon atoms and $R_2$ is hydrogen, methyl, or ethyl. Particularly this process provides methylaminomethylphosphonic acid dimethylesters and diethylesters, and the corresponding acid in high yield.

The known methylaminomethylphosphonic acid of the formula (II)

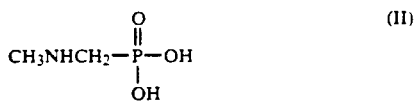

has interesting applications for fire proofing and as a herbicide; see, e.g., U.S.S.R. No. SU 1,074,886 (Chemical Abstracts, 100, 19374C (1984)) and Ger. Offen. No. 2,848,869 (Chemical Abstracts, 93, 39529Z (1980). Although several processes for the production of these N-substituted-aminomethylphosphonic acids have been patented and published, all of them are complicated with several disadvantages.

The process of U.S. Pat. No. 2,328,358 involves reaction of N-methyl-N-hydroxymethylstearamide with $PCl_3$, followed by the treatment with dilute hydrochloric acid to afford N-methylstearamidomethylphosphonic acid of the formula (III).

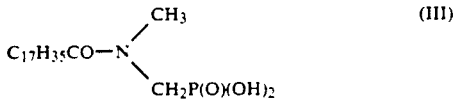

This is then hydrolyzed to methylaminomethylphosphonic acid. This process requires excessively lengthy reaction times. The use of stearamide makes this process bulky and expensive.

In U.S. Pat. No. 3,907,652, the N-tertiaryaminomethylphosphonic acid of the formula (IV)

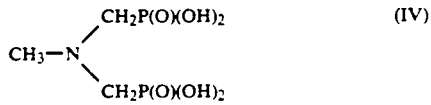

is prepared from methylamine, formaldehyde, and phosphorous acid ($H_3PO_3$) [Journal of Organic Chemistry, 31, 1603 (1966)] and followed by oxidative electrolysis to methylaminomethylphosphonic acid with removal of a phosphonomethyl group. This process requires special equipment for the latter reaction, which is done in strong acid.

The process of U.S. Pat. No. 4,351,779 involves the condensation of trimethylhexahydro-s-triazine with excess secondary dialkyl phosphite by heating at 20°-150° C., followed by hydrolysis or pyrolysis at high temperature (230°-240° C.). The source of phosphorus in this process, the secondary dialkylphosphite, is too expensive for commercial production.

In the process of U.S. Pat. No. 4,160,779, methylaminomethylphosphonic acid is prepared from the reaction of bis(chloromethyl)phosphonic acid in aqueous ammonia at 150° C. and 80 bars pressure for seven hours. This requires a high pressure autoclave, which is an expensive piece of equipment. Also, purification of the crude product requires an acid ion exchanger. These requirements make this process inadequate for large scale production.

Two other processes involve the reaction of amide with phosphorus trichloride. The disclosure by Tyka and Hagele [Synthesis, 218-19 (1984)] is a laboratory procedure for the synthesis of N-alkylaminomethylphosphonic acid from N-alkyl-N-hydroxymethylformamides with phosphorus trichloride. This procedure is disadvantageous for the preparation and isolation of N-alkyl-N-hydroxymethylformamide in view of its low yield, making it adequate for industrial use. Freeman claims in U.S. Pat. No. 4,830,788 that this problem is solved by making the amide having the formula V

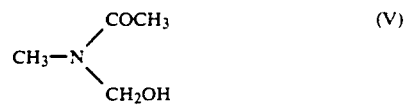

or its low molecular weight carboxylic ester as formula VI.

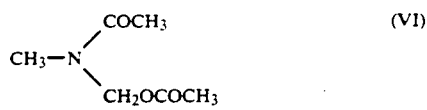

The amide for the production of methylaminomethylphosphonic acid is prepared in situ from N-methylacetamide, acetic acid, acetic anhydride, and paraformaldehyde by heating to 116° C. Then, the reaction mixture is cooled to 25° C. before adding phosphorus trichloride dropwise. Near the end of the $PCl_3$ addition, temperature is maintained at 59°-70° C. for forty five minutes and then gradually increased to 130° C. for 3 hours. This process requires too many reagents to be added and the control of the temperature affecting the yield of the reaction is too tedious. Furthermore, corrosive hydrogenchloride gas evolution is quite vigorous for several hours. For the purification of the reaction product, acetic acid coming from the hydrolysis of amide and acetyl chloride should be removed by distillation, which also makes this process laborious.

SUMMARY OF THE INVENTION

We now have discovered that a simple and mild process for the preparation of N-substituted aminomethylphosphonic acid derivatives in good yield provides the reaction of N-alkyl and N-cycloalkylhexahydro-s-triazine (formula VII)

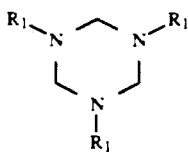

wherein $R_1$ is an alkyl having 1–18 carbon atoms, a cycloalkyl having 3–18 carbon atoms, such as methyl, ethyl, isopropyl, n-butyl, n-octyl, n-octadecyl and cyclohexyl with trialkylphosphites (formula VIII)

$$P(OR_2)_3 \qquad (VIII)$$

in the presence of titanium tetrachloride (TiCl$_4$) at $-20°$–$10°$ C. to yield N-substituted aminomethylphosphonic acid dialkylesters, followed by hydrolysis to yield good crystalline solid N-substituted aminomethylphosphonic acids.

Titanium tetrachloride is added to N-alkyl- or N-cycloalkyl-hexahydro-s-triazine in methylene chloride to give a dark red-colored solution. Into this solution is added trialkylphosphite and the resulting reaction mixture is stirred at $-20°$ to $20°$ C. After the reaction is completed, the reaction mixture is poured into ice slowly so as to not raise the temperature above 20° C. After the solution is neutralized with sat. NaHCO$_3$ solution, the reaction product is extracted with methylene chloride. The organic layer is washed with water and brine, and concentrated to give N-alkyl- and N-cycloalkylaminomethylphosphonic acid dialkyl esters in good yields. If desired, the corresponding acids can be obtained by hydrolysis without isolation of esters. The oily reaction product, N-substituted-aminomethylphosphonic acid dialkylester, is hydrolyzed by concentrated hydrochloric acid under reflux. A facile hydrolysis is also carried out with 1.5 mole equivalent of bromotrimethylsilane at room temperature. [cf. C. E. McKenna, et al., Tetrahedron Letters, 155 (1977)] After completion of the hydrolysis, all volatile solvents and byproducts are removed by distillation, followed by addition of low molecular weight alcohols, such as methanol, ethanol, or isopropanol, to crystallize the N-substituted-aminomethylphosphonic acids. The product is filtered and washed with low molecular weight alcohol to produce the crystalline product of N-substituted-aminomethylphosphonic acids in high yields and with high purity. The following examples illustrate the process of the invention in more detail.

EXAMPLE 1

Preparation of methylaminomethylphosphonic acid dimethylester and diethylester, and the corresponding acid To 12.9 g (0.1 mole) of trimethylhexahydro-s-triazine in 150 ml of methylene chloride was added 56.7 g (0.3 mole) of titanium tetrachloride at $-10°$ C., and the mixture was stirred for 10 minutes at $-10°$ C. To the resultant dark red solution was added 37.3 g (0.3 mole) of trimethylphosphite or 49.8 g (0.3 mole) of triethylphosphite. This reaction mixture was stirred at $-10°$–$10°$ C. for 1.5 hour. After the reaction was completed, it was poured into 200 g of ice slowly so as to not raise the temperature above 20° C. After the solution was neutralized with sat. NaHCO$_3$ solution, the reaction product was extracted with methylene chloride. After the removal of solvent, methylaminomethylphosphonic acid dimethylester or diethylester was isolated in 74 and 80% yield each. NMR spectra of purified dimethylester and diethylester of methylaminomethylphosphonic acid corresponded to their structures.

Analysis: C$_4$H$_{12}$NO$_3$P (153.11): Calculated: C 31.37 H 7.89 N 9.14 P 20.22%. Found: C 31.4 H 8.11 N 8.85 P 20.1%.

Analysis: C$_6$H$_{16}$NO$_3$P (181.17): Calculated: C 39.77 H 8.90 N 7.73 P 17.09%. Found: C 39.8 H 9.21 N 7.49 P 16.8%. Saponification was carried out by heating a solution of diethylester of methylaminomethylphosphonic acid with 100 ml of concentrated hydrochloric acid for 4 hours under reflux and then concentrating the reaction mixture to dryness. The oily residue was recrystallized from ethanol/water, affording 21.3 g (57%) of pure methylaminomethylphosphonic acid with a melting point of 272°–274° C. Hydrolysis of methylaminomethylphosphonic acid dimethylester gave the same product in 51% overall yield.

EXAMPLE 2

Preparation of ethylaminomethylphosphonic acid diethylester and of the corresponding acid In example 1, while otherwise proceeding as described, but substituting an equimolar quantity of triethylhexahydro-s-triazine for trimethylhexahydro-s-triazine, ethylaminomethylphosphonic acid diethylester was obtained in 84% yield.

Analysis: C$_7$H$_{18}$NO$_3$P (195.19): Calculated: C 43.07 H 9.29 N 7.17 P 15.86%. Found: C 44.2 H 9.44 N 7.51 P 14.9%.

Hydrolysis of the ester by the method described in example 1 gave a crystalline solid ethylaminomethylphosphonic acid in 58% overall yield. m.p. 276°–279° C.

EXAMPLE 3

Preparation of isopropylaminomethylphosphonic acid dimethylester and diethylester, and of the corresponding acid In example 1, while otherwise proceeding as described, but substituting an equimolar quantity of triisopropylhexahydro-s-triazine for trimethylhexahydro-s-triazine, isopropylaminomethylphosphonic acid dimethylester and diethylester were obtained in 68% and 71% yield each.

Analysis: C$_6$H$_{16}$NO$_3$P (181.17): Calculated: C 39.77 H 8.90 N 7.73%. Found: C 39.7 H 8.41 N 7.46%.

Analysis: C$_8$H$_{20}$NO$_3$P (209.22): Calculated: C 45.92 H 9.63 N 6.69 P 14.80%. Found: C 45.7 H 9.71 N 6.64 P 14.2%.

Hydrolysis of the diethylester by the method described in example 1 gave a crystalline solid ethylaminomethylphosphonic acid in 59% overall yield. m.p. 267°–269° C.

EXAMPLE 4

Preparation of n-butylaminomethylphosphonic acid diethylester and of the corresponding acid In example 1, while otherwise proceeding as described, but substituting an equimolar quantity of tri-n-butylhexahydro-s-triazine for trimethylhexahydro-s-triazine, n-butylaminomethylphosphonic acid diethylester was obtained in 86% yield.

Analysis: C$_9$H$_{22}$NO$_3$P (223.25): Calculated: C 48.42 H 9.93 N 6.27%. Found: C 44.9 H 9.83 N 6.12%.

Hydrolysis of the ester by the method described in example 1 gave a crystalline solid n-butylaminomethylphosphonic acid in 51% overall yield. m.p. 236°-240° C.

EXAMPLE 5

Preparation of n-octylaminomethylphosphonic acid dimethylester and of the corresponding acid In example 1, while otherwise proceeding as described, but changing quantities of tri-n-octylhexahydro-5-triazine (13.9 g, 30 mmole) for trimethylhexahydro-s-triazine, titanium tetrachloride (17.1 g, 90 mmole) and trimethylphosphine (11.2 g, 90 mmole), n-octylaminomethylphosphonic acid dimethylester was obtained in 91% yield.

Analysis: $C_{11}H_{26}NO_3P$ (251.30): Calculated: C 52.57 H 10.42 N 5.57%. Found: C 52.9 H 10.9 N 5.15%.

n-Octylaminomethylphosphonic acid was obtained in 66% overall yield by saponification of dimethylester with 40 ml of concentrated hydrochloric acid under reflux, followed by recrystallization in isopropanol/water. m.p. 262°-265° C.

EXAMPLE 6

Preparation of n-octadecylaminomethylphosphonic acid dimethylester and of the corresponding acid In example 1, while otherwise proceeding as described, but changing quantities of tri-n-octadecylhexahydro-s-triazine (8.4 g, 10 mmole), titanium tetrachloride (5.7 g, 30 mmole) and trimethylphosphine (3.7 g, 30 mmole), n-octadecylaminomethylphosphonic acid dimethylester was obtained in 85% yield.

Analysis: $C_{21}H_{46}NO_3P$ (391.57): Calculated: C 64.41 H 11.84 N 3.57%. Found: C 64.8 H 12.1 N 3.61%. A crystalline solid n-octadecylaminomethylphosphonic acid was obtained in 49% overall yield by saponification of dimethylester with 20 ml of concentrated hydrochloric acid under reflux, followed by recrystallization in isopropanol/water. water. m.p. 110°-112° C.

EXAMPLE 7

Preparation of cyclohexylaminomethylphosphonic acid dimethylester and diethylester, and of the corresponding acid In example 1, while otherwise proceeding as described, but substituting an equimolar quantity of tricyclohexylhexahydro-s-triazine for trimethylhexahydro-s-triazine, cyclohexylaminomethylphosphonic acid dimethylester and diethylester were obtained in 78% and 81% each.

Analysis: $C_9H_{20}NO_3P$ (221.23): Calculated: C 48.86 H 9.11 N 6.33%. Found: C 48.6 H 8.99 N 6.62%.

Analysis: $C_{11}H_{24}NO_3P$ (249.28): Calculated: C 52.99 H 9.70 N 5.61%. Found: C 52.6 H 9.71 N 5.47%.

Hydrolysis of the diethylester by the method described in example 1 gave a crystalline solid cyclohexylaminomethylphosphonic acid in 61% overall yield. m.p. 281°-284° C.

What is claimed is:

1. A process for the preparation of N-alkyl-substituted-aminomethyl-phosphonic acid derivatives of the formula (I) which comprises reacting triazines of the formula (II) with trialkyl phosphites of the formula (III) in the presence of titanium tetrachloride and methylene chloride at about −20° C. to about 20° C.

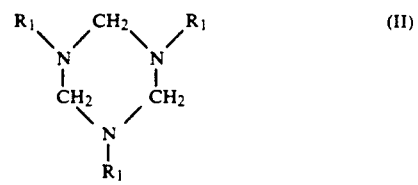

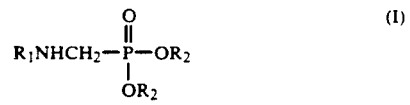

wherein $R_1$ is methyl, ethyl, isopropyl, n-butyl, n-octyl, n-octadecyl, or cyclohexyl; and $R_2$ is hydrogen, methyl, or ethyl, with the proviso that $R_2$ is methyl or ethyl in the formula (III).

2. The process according to claim 1 wherein triazines of the formula (II) and titanium tetrachloride and trialkyl phosphites of the formula (III) are added in a molar ratio of 1:3:3.

3. The process according to claim 1 wherein for the preparation of N-alkyl-substituted-aminomethylphosphonic acid in which $R_2$ is hydrogen, the reaction product is added to concentrated hydrochloric acid and heated under reflux for 4 hours or the reaction product is added to 1.5 mol equivalent of bromotrimethyl silane and allowed to stand at 20° C.

* * * * *

UNITED STATES PATENT AND TRADEMARK OFFICE
CERTIFICATE OF CORRECTION

PATENT NO.  : 5,099,056
DATED       : March 24, 1992
INVENTOR(S) : Hyun-Joon HA and Gong-Sil NAM It is certified that error appears in the above-identified patent and that said Letters Patent is hereby corrected as shown below:

ON THE TITLE PAGE:

[57] ABSTRACT, first and second lines of text, delete "aminoethylohosphonic" and substitute therefor -- aminomethylphosphonic --.

[57] ABSTRACT, second column, second line after formula (I), delete "cycloolkyl" and substitute therefor -- cycloalkyl --.

IN THE SPECIFICATION:

Column 2, line 28, delete "adequate" and substitute therefor -- inadequate --.

Signed and Sealed this

Eighth Day of June, 1993

Attest:

MICHAEL K. KIRK

Attesting Officer

Acting Commissioner of Patents and Trademarks